US012589383B2

(12) United States Patent
Xiong et al.

(10) Patent No.: US 12,589,383 B2
(45) Date of Patent: Mar. 31, 2026

(54) SPHERICAL TITANIUM SILICALITE MOLECULAR SIEVE CATALYST AND PREPARATION METHOD THEREFOR

(71) Applicant: Shanghai Huayi New Material Co., Ltd, Shanghai (CN)

(72) Inventors: Desheng Xiong, Shanghai (CN); Yan Zhuang, Shanghai (CN); Congguang Luo, Shanghai (CN); Yao Cui, Shanghai (CN); Xiaodong Chu, Shanghai (CN)

(73) Assignee: Shanghai Huayi New Material Co., Ltd, Shanghai (CN)

( * ) Notice: Subject to any disclaimer, the term of this patent is extended or adjusted under 35 U.S.C. 154(b) by 471 days.

(21) Appl. No.: 18/270,427

(22) PCT Filed: Nov. 2, 2021

(86) PCT No.: PCT/CN2021/128086
§ 371 (c)(1),
(2) Date: Jun. 29, 2023

(87) PCT Pub. No.: WO2022/142710
PCT Pub. Date: Jul. 7, 2022

(65) Prior Publication Data
US 2024/0100512 A1     Mar. 28, 2024

(30) Foreign Application Priority Data
Dec. 29, 2020     (CN) .......................... 202011589175.2

(51) Int. Cl.
B01J 29/89          (2006.01)
B01J 35/08          (2006.01)
(Continued)

(52) U.S. Cl.
CPC ............... B01J 29/89 (2013.01); B01J 35/51 (2024.01); B01J 37/0018 (2013.01);
(Continued)

(58) Field of Classification Search
None
See application file for complete search history.

(56) References Cited

U.S. PATENT DOCUMENTS 4,410,501 A     10/1983  Taramasso et al.
4,701,428 A     10/1987  Bellussi et al.
(Continued)

FOREIGN PATENT DOCUMENTS

CN          101157051 A      4/2008
CN          102249863 A      11/2011
(Continued)

OTHER PUBLICATIONS

Wang et al., Research on Al-Sols and Alumina-Washcoating—II The Properties of Alumina-Washcoating Carrier, Journal of Beijing University of Technology, 2002, 28(1):58-61.
(Continued)

*Primary Examiner* — Yun Qian
(74) *Attorney, Agent, or Firm* — Quarles & Brady LLP

(57) ABSTRACT

In a spherical titanium silicalite catalyst and a preparation method therefor, the spherical titanium silicalite catalyst has the following composition: $xTiO_2 \cdot (1-x)SiO_2/yMPO_4$, wherein x is equal to 0.0005-0.04, y is equal to 0.005-0.20, M is a metal element selected from alkaline earth metals, transition metals or combinations of two or more thereof. The spherical titanium silicalite catalyst is prepared by the following method: (i) providing titanium silicalite raw powder with the composition of $xTiO_2 \cdot (1-x)SiO_2$, wherein x is equal to 0.0005-0.04, and y is equal to 0.005-0.20; (ii) mixing silica sol, an organic template agent and phosphate
(Continued)

in proportion to obtain an adhesive; and (iii) mixing the adhesive with the titanium silicalite raw powder, and carrying out spray-drying molding and firing to obtain the titanium silicalite catalyst.

17 Claims, 1 Drawing Sheet

(51) Int. Cl.
| | |
|---|---|
| *B01J 35/51* | (2024.01) |
| *B01J 37/00* | (2006.01) |
| *C01B 39/08* | (2006.01) |
| *C07C 37/00* | (2006.01) |
| *B01J 35/34* | (2024.01) |

(52) U.S. Cl.
CPC ......... *B01J 37/0045* (2013.01); *C01B 39/085* (2013.01); *C07C 37/001* (2013.01); *B01J 35/34* (2024.01); *B01J 2235/30* (2024.01); *C01P 2004/03* (2013.01)

(56) References Cited

U.S. PATENT DOCUMENTS 5,500,199 A    3/1996   Bellussi et al.

| | | |
|---|---|---|
| 6,153,552 A | 11/2000 | Wachter et al. |
| 2009/0042718 A1 | 2/2009 | Kaminsky et al. |
| 2013/0149235 A1 | 6/2013 | Shen et al. |

FOREIGN PATENT DOCUMENTS

| | | |
|---|---|---|
| CN | 103212435 A | 7/2013 |
| CN | 104368382 A | 2/2015 |
| CN | 106964400 A | 7/2017 |
| CN | 111085265 A | 5/2020 |
| CN | 111115653 A | 5/2020 |
| CN | 112774726 A | 5/2021 |
| EP | 0265018 A2 | 4/1988 |

OTHER PUBLICATIONS

Yi et al., Synthesis of Mn-CeOx/Cordierite Catalysts using Various Coating Materials and Pore-Forming Agents for Non-Methane Hydrocarbon Oxidation in Cooking Oil Fumes, Ceramics International, 2018, 44(13), 18 pages.
The State Intellectual Property Office of People's Republic of China, Notification to Grant Patent Right for Invention and Search Report, Application No. 202011589175.2, Jun. 29, 2022, 5 pages.
PCT International Search Report and Written Opinion, PCT/CN2021/128086, Feb. 7, 2022, 14 pages.
European Patent Office, Extended European Search Report, Application No. 21913454.1, Nov. 26, 2024, 8 pages.

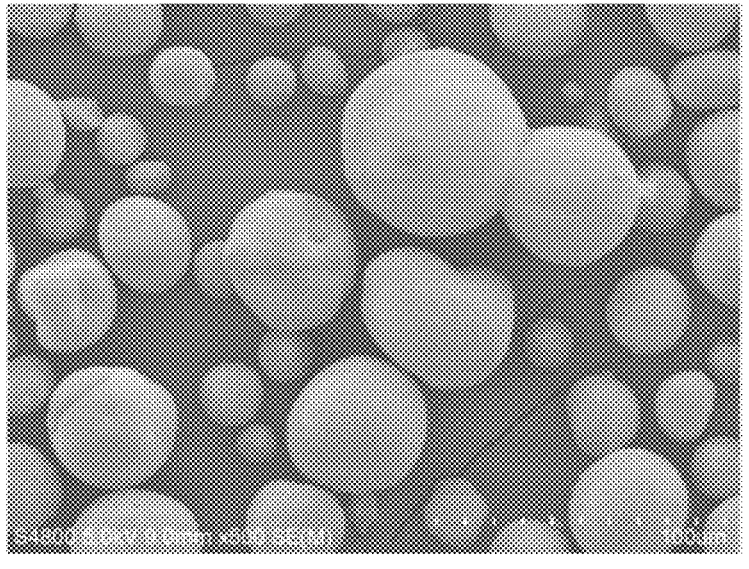

1

SPHERICAL TITANIUM SILICALITE MOLECULAR SIEVE CATALYST AND PREPARATION METHOD THEREFOR

CROSS-REFERENCE TO RELATED APPLICATION

This application represents the U.S. national stage entry of International Application No. PCT/CN2021/128086 filed Nov. 2, 2021, which claims priority to Chinese Application No. 202011589175.2 filed Dec. 29, 2020, the disclosure of which is incorporated herein by reference in its entirety and for all purposes.

TECHNICAL FIELD

The present invention relates to a spherical titanium silicalite catalyst, a method for preparing the same and use of the same in hydroxylation of phenol to hydroquinone.

BACKGROUND ART

Hydroquinone and catechol are two important chemical raw materials and chemical intermediates, and they are widely used. Catechol may be used as a rubber hardener, an electroplating additive, an antiseptic and a fungicide for skin, a hair dye, a photographic developer, an antioxidant for color photography, a dye and a color developer for fur, and an anti-peeling agent for paint and varnish. Hydroquinone is mainly used in developers, anthraquinone dyes, azo dyes, synthetic ammonia cosolvents, rubber anti-aging agents, polymerization inhibitors, stabilizers for coatings and flavors, and antioxidants.

At present, the industrial technologies for producing hydroquinone include the cumene process, the phenol hydroxylation process and the aniline process. Among them, the phenol hydroxylation process employs phenol as a raw material and hydrogen peroxide as an oxidant, and hydroquinone and catechol are obtained by hydroxylation reactions. The by-product is water, so this is a green process route. The catalysts used in the phenol hydroxylation process include homogeneous iron catalysts, perchloric acid catalysts and solid titanium silicalite catalysts. In the early 1980s, Taramasso from Italy disclosed a new type of catalytic oxidation material called titanium silicalite (TS-1) in U.S. Pat. No. 4,410,501. When it was used in the phenol hydroxylation process, it exhibited good catalytic activity and selectivity.

However, since the original crystal grains of the titanium silicalite are small (100-500 nm), it is not conducive to separation and recovery of the catalyst and the product during industrial operation. Hence, it is necessary to further form the titanium silicalite catalyst into a microspherical titanium silicalite catalyst. Conventional forming processes include bar extrusion and spraying. The bar extruded catalyst is suitable for a fixed bed reactor, and the spraying is suitable for a slurry bed process. The spraying is the main process for preparing a microspherical titanium silicalite catalyst. U.S. Pat. No. 5,500,199, EP00265018, and U.S. Pat. No. 4,701,428 all describe the spray-drying forming process.

For example, as described in Example 1 in U.S. Pat. No. 4,701,428, firstly, an original powder of titanium silicalite is obtained by centrifugation, and tetraethyl orthosilicate and tetrapropylammonium hydroxide are formulated into an aqueous solution. Then, they are mixed and sprayed to form a microspherical titanium silicalite catalyst.

Although spray-drying can advantageously prepare a microspherical titanium silicalite catalyst, it is found that the performance of the microspherical titanium silicalite prepared by spraying is worse than that of the original powder of the titanium silicalite before forming. Moreover, the strength of the spherical titanium silicalite with silica as a binder is still not very good. During the long-term operation, the spherical particles are broken, and a large number of fine particles are produced. These particles will be lost by passing through a filter screen during the separation process, leading to increased catalyst consumption.

In order to solve the above problems, CN103212435A proposes a method for preparing a spherical titanium silicalite, wherein a secondary crystallization process is added to directionally transform the amorphous silicon dioxide binder on the surface of the spray-formed microspherical titanium silicalite catalyst into crystalline silicon dioxide, thereby promoting the catalytic oxidation activity of the microspherical titanium silicalite, and also ensuring the mechanical strength of the microspherical titanium silicalite. However, the preparation process of this method is complicated, and the mechanical strength of the formed titanium silicalite is still not very high.

CN111115653A discloses a modified method for forming a spray-formed microspherical titanium silicalite, including a molecular sieve forming step and a catalyst modification step. The molecular sieve forming step comprises:

(1) Preparation of spray mother liquor: adding a silica sol and a pore-forming agent to a molecular sieve mother liquor to obtain mother liquor A, and adjusting the pH of mother liquor A to 9-10 with concentrated nitric acid, wherein the molecular sieve mother liquor comprises a titanium silicalite;

Adding a titanium source dropwise to tert-butanol, stirring for 30 minutes, then adding it to mother liquor A, and aging at 50° C. for 24 hours under stirring to obtain mother liquor B;

(2) Forming of molecular sieve: mother liquor B is spray-dried to obtain a formed molecular sieve, wherein an inlet temperature of the spray-drying process is 180-200° C., and an outlet temperature is 100-105° C.

This molecular sieve forming process is complicated, leading to high cost.

Therefore, there is still a need to provide a method for preparing a spherical titanium silicalite catalyst. The catalyst prepared by this method has a catalytic activity similar to that of the original powder of the titanium silicalite, and the mechanical strength of the microspherical titanium silicalite is good, so that its structural stability can be maintained during long-term catalytic reaction. There is also a need to provide the spherical titanium silicalite catalyst prepared by the above method.

SUMMARY

Therefore, one aspect of the present invention is directed to a microspherical titanium silicalite catalyst having the following composition:

$$xTiO_2 \cdot (1-x)SiO_2/yMPO_4$$

wherein x=0.0005-0.04, y=0.005-0.2;

M is a metallic element selected from alkaline earth metals, transition metals, or combinations of two or more thereof;

it is prepared as follows:

(i) providing an original titanium silicalite powder, wherein the original titanium silicalite powder has following composition:

$$xTiO_2 \cdot (1-x)SiO_2$$

wherein x=0.0005-0.04;

(ii) mixing a silica sol, an organic template and a phosphate at a molar ratio of 1:0.02-0.2:0.01-0.5 of $SiO_2$:organic template:phosphate to obtain a binder, wherein the phosphate is selected from alkaline earth metal phosphates, transition metal phosphates, or combinations of two or more thereof;

(iii) mixing the binder with the original titanium silicalite powder, spray-drying and firing to obtain a titanium silicalite catalyst, wherein when the binder is mixed with the original titanium silicalite powder, a weight ratio of silicon dioxide in the binder to the original titanium silicalite powder is 1:2-20.

Another aspect of the present invention is directed to a method for preparing a microspherical titanium silicalite catalyst, wherein the microspherical titanium silicalite catalyst has the following composition:

$$xTiO_2 \cdot (1-x)SiO_2/yMPO_4$$

wherein x=0.0005-0.04, y=0.005-0.2;

M is selected from alkaline earth metals, transition metals, or combinations of two or more thereof;

the method comprises:

(i) providing an original titanium silicalite powder, wherein the original titanium silicalite powder has following composition:

$$xTiO_2 \cdot (1-x)SiO_2$$

wherein x=0.0005-0.04;

(ii) mixing a silica sol, an organic template and a phosphate at a molar ratio of 1:0.02-0.2:0.01-0.5 of $SiO_2$:organic template:phosphate to obtain a binder, wherein the phosphate is selected from alkaline earth metal phosphates, transition metal phosphates, or combinations of two or more thereof;

(iii) mixing the binder with the original titanium silicalite powder, spray-drying and firing to obtain a titanium silicalite catalyst, wherein when the binder is mixed with the original titanium silicalite powder, a weight ratio of silicon dioxide in the binder to the original titanium silicalite powder is 1:2-20.

DESCRIPTION OF THE DRAWING

Now, the present invention will be further illustrated with reference to the following accompanying drawing in which:

FIG. 1 is an SEM image of a microspherical titanium silicalite according to an embodiment of the present invention.

DETAILED DESCRIPTION

The microspherical titanium silicalite catalyst of the present invention has the following composition:

$$xTiO_2 \cdot (1-x)SiO_2/yMPO_4$$

wherein x=0.0005-0.04, preferably 0.001-0.035, more preferably 0.002-0.030, still more preferably 0.003-0.025, yet more preferably 0.004-0.020, most preferably 0.005-0.01;

y=0.005-0.2, preferably 0.008-0.15, more preferably 0.012-0.010, still preferably 0.015-0.08, most preferably 0.03-0.05;

M is selected from alkaline earth metals, transition metals, or combinations of two or more thereof.

In an embodiment of the present invention, M is selected from calcium, magnesium, zinc, nickel, aluminum, iron, copper, cobalt, or combinations of two or more thereof.

In an embodiment of the present invention, the microspherical titanium silicalite catalyst has an average particle size (i.e. D50 particle size) of 10-50 microns, preferably 13-47 microns, more preferably 16-44 microns, still preferably 20-40 microns, most preferably 25-35 microns.

The method for preparing the microspherical titanium silicalite catalyst of the present invention comprises the following steps:

(i) An original titanium silicalite powder is provided, wherein the original titanium silicalite powder has following composition:

$$xTiO_2 \cdot (1-x)SiO_2$$

wherein x=0.0005-0.04, preferably 0.001-0.035, more preferably 0.002-0.030, still more preferably 0.003-0.025, yet more preferably 0.004-0.020, most preferably 0.005-0.01.

The method for providing the original titanium silicalite powder is not particularly limited, and may be a conventional method known in the art. For example, the method disclosed by U.S. Pat. No. 4,410,501 may be used to provide the original titanium silicalite powder.

In an embodiment of the present invention, the method for providing the original titanium silicalite powder comprises the following steps:

Adding tetraethyl orthosilicate and tetraethyl titanate to a reaction vessel equipped with a stirrer in a carbon dioxide-free environment, then gradually adding a tetraethylammonium hydroxide solution, stirring, and heating to 80-90° C. to accelerate hydrolysis and evaporate the resultant ethanol; then adding water, transferring the reactant to a titanium reactor with a stirrer, heating to 170-180° C., stirring at this temperature for 9-12 days, and washing to obtain a crystalline product; and finally, firing the product at a temperature of 500-600° C. for 5-7 hours to obtain an original titanium silicalite powder.

(ii) A silica sol, an organic template and a phosphate are mixed at a molar ratio of 1:0.02-0.2:0.01-0.5 of $SiO_2$:organic template:phosphate to obtain a binder, wherein the phosphate is selected from alkaline earth metal phosphates, transition metal phosphates, or combinations of two or more thereof.

In the binder of the present invention, the molar ratio of silica sol to organic template ($SiO_2$:organic template) is 1:0.02-0.2, preferably 1:0.04-0.18, more preferably 1:0.06-0.16, still more preferably 1:0.08-0.14, most preferably 1:0.1-0.12.

In the binder of the present invention, the molar ratio of silica sol to phosphate ($SiO_2$:phosphate) is 1:0.01-0.5, preferably 1:0.04-0.45, more preferably 1:0.08-0.4, still more preferably 1:0.1-0.35, most preferably 1:0.15-0.3.

The organic template suitable for the method of the present invention is not particularly limited, and may be a conventional organic template known in the art. In an embodiment of the present invention, the organic template is selected from alkylammonium halides, for example: $R_{10-20}(R_{1-4})_3$ ammonium halides, such as cetyltrimethylammonium bromide, cetyltriethylammonium bromide, cetyldiethylmethylammonium bromide, cetyltrimethylammonium chloride, cetyltriethylammonium chloride, cetyldiethylmethylammonium chloride, or mixtures thereof.

The phosphate used in the present invention is selected from alkaline earth metal phosphates, transition metal phosphates or combinations of two or more thereof. In an embodiment of the present invention, the phosphate is selected from zinc phosphate, aluminum dihydrogen phosphate, aluminum hydrogen phosphate, aluminum phosphate, magnesium phosphate, calcium phosphate, nickel phosphate, ferric phosphate, copper phosphate, cobalt phosphate or a combination of two or more thereof, preferably selected from zinc phosphate, aluminum dihydrogen phosphate, magnesium phosphate, calcium phosphate or a combination of two or more thereof.

The method for mixing the silica sol, the organic template and the phosphate at the ratio is not particularly limited, and may be a conventional mixing method known in the art.

(iii) The binder is mixed with the original titanium silicalite powder, spray-dried and fired to obtain a titanium silicalite catalyst, wherein when the binder is mixed with the original titanium silicalite powder, a weight ratio of silicon dioxide in the binder to the original titanium silicalite powder is 1:2-20.

The method of the present invention comprises the step of mixing the binder with the original titanium silicalite powder. Based on the weight of silicon dioxide in the binder, the ratio of the binder to the original titanium silicalite powder is 1:2-20, preferably 1:4-18, more preferably 1:6-16, still more preferably 1:8-14, most preferably 1:10-12.

The method for mixing the binder with the original titanium silicalite powder is not particularly limited, as long as they can be mixed evenly.

The spray-drying method suitable for the present invention is not particularly limited, and may be a conventional method known in the art. For example, the spray-drying method disclosed by CN111115653A may be used. In an embodiment of the present invention, the sprayer has an inlet temperature of 180-200° C. and an outlet temperature of 100-105° C. during spray drying.

After spray-drying, the method of the present invention comprises a firing step. The applicable firing process is not particularly limited, and may be a conventional firing process known in the art. In an embodiment of the present invention, the firing is carried out in air, and the firing temperature is 350-600° C., preferably 380-560° C., more preferably 400-530° C.

In a preferred embodiment of the present invention, the method for preparing the microspherical titanium silicalite catalyst of the present invention comprises:

(i) Synthesis of titanium silicalite TS-1 according to the method disclosed by U.S. Pat. No. 4,410,501: mixing and crystallizing the slurry at a predetermined molar ratio of $TiO_2$:$SiO_2$:TPAOH:$H_2O$; separating the slurry by high-speed centrifugation after crystallization; then re-dispersing the solid in water, washing several times with water, and then drying to obtain an original titanium silicalite TS-1 powder containing the template, wherein the particle size of the original powder is 200-300 nm;

(ii) mixing silica sol, cetyltrimethylammonium bromide, and phosphate uniformly at a predetermined ratio to form a binder solution containing the template and phosphate; and then adding the original titanium silicalite powder containing the template to the mixed solution and stirring;

(iii) spray-drying the above mixed solution to obtain a spherical titanium silicalite catalyst intermediate;

(3) Calcining the spherical titanium silicalite intermediate in a calcinator (such as a muffle furnace) to obtain a spherical titanium silicalite catalyst.

The method for preparing the spherical titanium silicalite catalyst of the present invention comprises mixing an organic template, a phosphate, a silica sol binder, and an original titanium silicalite powder uniformly, followed by spraying and calcination to obtain the microspherical titanium silicalite. The catalytic activity of the catalyst is similar to that of the original titanium silicalite powder, while the microspherical titanium silicalite has better mechanical strength and can maintain structural stability during long-term catalytic reaction.

The spherical titanium silicalite catalyst of the present invention can be used for hydroxylation of phenol to benzenediols. In an embodiment of the present invention, the catalytic reaction of said hydroxylation of phenol to benzenediols comprises the following steps:

Reacting phenol with hydrogen peroxide in a reactor at ambient pressure, 30-90° C., a phenol concentration of 5-50%, and a molar ratio of phenol to $H_2O_2$ of 10-1; and after the reaction, filtering the reaction solution through filter cloth to separate the spherical titanium silicalite which is recycled to the reactor for next reaction.

The catalytic activity of the spherical titanium silicalite catalyst prepared by the method of the present invention is similar to that of the original titanium silicalite powder, while the spherical titanium silicalite has better mechanical strength and can maintain structural stability during long-term catalytic reaction.

The present invention will be illustrated in more detail with reference to the following Examples.

Example 1

Preparation of Original Titanium Silicalite Powder:

Titanium silicalite TS-1 was synthesized according to the method disclosed by U.S. Pat. No. 4,410,501. In the synthesis, the molar ratio of $TiO_2$:$SiO_2$:TPAOH:$H_2O$ was 0.03:1:0.20:20. After crystallization, the slurry was separated by high-speed centrifugation. Then, the solid was re-dispersed in water, washed several times with water, and then dried to obtain an original titanium silicalite TS-1 powder containing the template. The particle size of the original powder was 200-300 nm.

Preparation of Spherical Titanium Silicalite Catalyst:

(1) Silica sol, cetyltrimethylammonium bromide and zinc phosphate were mixed uniformly at a molar ratio of 1:0.1:0.1 of $SiO_2$ in silica sol (30% concentration): cetyltrimethylammonium bromide:zinc phosphate to form a binder solution containing the template and phosphate. Then, the original titanium silicalite powder containing the template was added to the mixed solution at a weight ratio of 1:10 of $SiO_2$:original powder. Vigorous stirring was conducted at 30° C. for 2 hours.

(2) The above mixed solution was spray-dried to obtain a spherical titanium silicalite catalyst intermediate having a $D_{50}$ of 35 microns.

(3) The spherical titanium silicalite intermediate was calcined in a muffle furnace. The calcination atmosphere was air, and the calcination temperature was 500° C. After calcination, a spherical titanium silicalite catalyst was obtained.

The SEM image of the prepared microspherical titanium silicalite is shown in FIG. 1.

Example 2

The original titanium silicalite powder was synthesized according to the same method as described in Example 1.

The spherical titanium silicalite catalyst was synthesized according to the following method:

(1) Silica sol, cetyltrimethylammonium bromide and aluminum dihydrogen phosphate were mixed uniformly at a molar ratio of 1:0.1:0.1 of $SiO_2$ in silica sol (30% concentration):cetyltrimethylammonium bromide:aluminum dihydrogen phosphate to form a binder solution. Then, the original titanium silicalite powder containing the template was added to the mixed solution at a weight ratio of 1:10 of $SiO_2$:original powder. Vigorous stirring was conducted at 30° C. for 2 hours.

(2) The above mixed solution was spray-dried to obtain a spherical titanium silicalite catalyst intermediate having a $D_{50}$ of 48 microns.

(3) The spherical titanium silicalite intermediate was calcined in a muffle furnace. The calcination atmosphere was air, and the calcination temperature was 550° C. After calcination, a spherical titanium silicalite catalyst was obtained.

Example 3

The original titanium silicalite powder was synthesized according to the same method as described in Example 1.

The spherical titanium silicalite catalyst was synthesized according to the following method:

(1) Silica sol, cetyltrimethylammonium chloride and aluminum dihydrogen phosphate were mixed uniformly at a molar ratio of 1:0.15:0.1 of $SiO_2$ in silica sol (30% concentration):cetyltrimethylammonium chloride:aluminum dihydrogen phosphate to form a binder solution. Then, the original titanium silicalite powder containing the template was added to the mixed solution at a weight ratio of 1:10 of $SiO_2$:original powder. Vigorous stirring was conducted at 30° C. for 2 hours.

(2) The above mixed solution was spray-dried to obtain a spherical titanium silicalite catalyst intermediate having a $D_{50}$ of 47 microns.

(3) The spherical titanium silicalite intermediate was calcined in a muffle furnace. The calcination atmosphere was air, and the calcination temperature was 550° C. After calcination, a spherical titanium silicalite catalyst was obtained.

Example 4

The original titanium silicalite powder was synthesized according to the same method as described in Example 1.

The spherical titanium silicalite catalyst was synthesized according to the following method:

(1) Silica sol, cetyltrimethylammonium chloride and magnesium phosphate were mixed uniformly at a molar ratio of 1:0.15:0.18 of $SiO_2$ in silica sol (30% concentration):cetyltrimethylammonium chloride:magnesium phosphate to form a binder solution. Then, the original titanium silicalite powder containing the template was added to the mixed solution at a weight ratio of 1:5 of $SiO_2$:original powder. Vigorous stirring was conducted at 30° C. for 2 hours.

(2) The above mixed solution was spray-dried to obtain a spherical titanium silicalite catalyst intermediate having a $D_{50}$ of 32 microns.

(3) The spherical titanium silicalite intermediate was calcined in a muffle furnace. The calcination atmosphere was air, and the calcination temperature was 580° C. After calcination, a spherical titanium silicalite catalyst was obtained.

Example 5

The original titanium silicalite powder was synthesized according to the same method as described in Example 1.

The spherical titanium silicalite catalyst was synthesized according to the following method:

(1) Silica sol, cetyltrimethylammonium bromide and calcium phosphate were mixed uniformly at a molar ratio of 1:0.15:0.05 of $SiO_2$ in silica sol (30% concentration): cetyltrimethylammonium bromide:calcium phosphate to form a binder solution. Then, the original titanium silicalite powder containing the template was added to the mixed solution at a weight ratio of 1:10 of $SiO_2$: original powder. Vigorous stirring was conducted at 30° C. for 2 hours.

(2) The above mixed solution was spray-dried to obtain a spherical titanium silicalite catalyst intermediate having a $D_{50}$ of 42 microns.

(3) The spherical titanium silicalite intermediate was calcined in a muffle furnace. The calcination atmosphere was air, and the calcination temperature was 500° C. After calcination, a spherical titanium silicalite catalyst was obtained.

Example 6

The original titanium silicalite powder was synthesized according to the same method as described in Example 1.

The spherical titanium silicalite catalyst was synthesized according to the following method:

(1) Silica sol, cetyltrimethylammonium bromide and aluminum dihydrogen phosphate were mixed uniformly at a molar ratio of 1:0.15:0.04 of $SiO_2$ in silica sol (30% concentration):cetyltrimethylammonium bromide:aluminum dihydrogen phosphate to form a binder solution. Then, the original titanium silicalite powder containing the template was added to the mixed solution at a weight ratio of 1:15 of $SiO_2$:original powder. Vigorous stirring was conducted at 30° C. for 2 hours.

(2) The above mixed solution was spray-dried to obtain a spherical titanium silicalite catalyst intermediate having a $D_{50}$ of 28 microns.

(3) The spherical titanium silicalite intermediate was calcined in a muffle furnace. The calcination atmosphere was air, and the calcination temperature was 500° C. After calcination, a spherical titanium silicalite catalyst was obtained.

Example 7

The original titanium silicalite powder was synthesized according to the same method as described in Example 1.

The spherical titanium silicalite catalyst was synthesized according to the following method:

(1) Silica sol, cetyltrimethylammonium bromide and aluminum dihydrogen phosphate were mixed uniformly at a molar ratio of 1:0.15:0.4 of $SiO_2$ in silica sol (30% concentration):cetyltrimethylammonium bromide:aluminum dihydrogen phosphate to form a binder solution. Then, the original titanium silicalite powder containing the template was added to the mixed solution at a weight ratio of 1:15 of $SiO_2$:original powder. Vigorous stirring was conducted at 30° C. for 2 hours.

(2) The above mixed solution was spray-dried to obtain a spherical titanium silicalite catalyst intermediate having a $D_{50}$ of 55 microns.

(3) The spherical titanium silicalite intermediate was calcined in a muffle furnace. The calcination atmosphere was air, and the calcination temperature was 500° C. After calcination, a spherical titanium silicalite catalyst was obtained.

Comparative Example 1

The original titanium silicalite powder was synthesized according to the same method as described in Example 1. Then, the original catalyst powder was calcined at 550° C. in an air atmosphere to obtain an unformed titanium silicalite TS-1.

Comparative Example 2

The original titanium silicalite powder was synthesized according to the same method as described in Example 1.

The spherical titanium silicalite catalyst was synthesized according to the following method:

(1) The titanium silicalite was added to silica sol at a weight ratio of 1:10 of $SiO_2$ in silica sol (30% concentration):original titanium silicalite powder, and mixed uniformly.

(2) The above mixed solution was spray-dried to obtain a spherical titanium silicalite catalyst intermediate having a $D_{50}$ of 37 microns.

(3) The spherical titanium silicalite intermediate was calcined in a muffle furnace. The calcination atmosphere was air, and the calcination temperature was 500° C. After calcination, a spherical titanium silicalite catalyst was obtained.

Comparative Example 3

The original titanium silicalite powder was synthesized according to the same method as described in Example 1.

The spherical titanium silicalite catalyst was synthesized according to the following method:

(1) Silica sol and aluminum dihydrogen phosphate were mixed uniformly at a molar ratio of 1:0.4 of $SiO_2$ in silica sol (30% concentration):aluminum dihydrogen phosphate to form a binder solution. Then, the original titanium silicalite powder containing the template was added to the mixed solution at a weight ratio of 1:15 of $SiO_2$:original powder. Vigorous stirring was conducted at 30° C. for 2 hours.

(2) The above mixed solution was spray-dried to obtain a spherical titanium silicalite catalyst intermediate having a $D_{50}$ of 52 microns.

(3) The spherical titanium silicalite intermediate was calcined in a muffle furnace. The calcination atmosphere was air, and the calcination temperature was 500° C. After calcination, a spherical titanium silicalite catalyst was obtained.

Comparative Example 4

The original titanium silicalite powder was synthesized according to the same method as described in Example 1.

The spherical titanium silicalite catalyst was synthesized according to the following method:

(1) Silica sol and cetyltrimethylammonium bromide were mixed uniformly at a molar ratio of 1:0.15 of $SiO_2$ in silica sol (30% concentration):cetyltrimethylammonium bromide to form a binder solution. Then, the original titanium silicalite powder containing the template was added to the mixed solution at a weight ratio of 1:15 of $SiO_2$:original powder. Vigorous stirring was conducted at 30° C. for 2 hours.

(2) The above mixed solution was spray-dried to obtain a spherical titanium silicalite catalyst intermediate having a $D_{50}$ of 28 microns.

(3) The spherical titanium silicalite intermediate was calcined in a muffle furnace. The calcination atmosphere was air, and the calcination temperature was 500° C. After calcination, a spherical titanium silicalite catalyst was obtained.

Example 8

The catalysts of Examples 1-7 and Comparative Examples 1-4 were tested for their performance in catalyzing hydroxylation of phenol to hydroquinone. The reaction was carried out under mechanical stirring in a three-neck round bottom flask equipped with a reflux condenser and heated with a thermostatic water bath. The reaction pressure was ambient pressure; the reaction temperature was 70° C.; the phenol concentration was 50%, the mass ratio of catalyst to phenol was 1:20, and the molar ratio of phenol to $H_2O_2$ was 3:1. Hydrogen peroxide was slowly added dropwise through a peristaltic pump. The reaction time was 6 hours. After the reaction was completed, filter cloth with an average pore size of 1 micron was used to centrifuge the reaction solution. A small amount of fine titanium silicalite particles were lost through the filter cloth during filtration. The filtered solid was recycled to the flask for next reaction.

The contents of phenol, catechol and hydroquinone in the reaction solution were analyzed by liquid chromatography.

The conversion of phenol was calculated according to the following formula:

$$\text{Conversion} = 1 - \frac{m_{phenol\ after\ reaction}}{m_{phenol\ before\ reaction}}$$

The effective utilization rate of hydrogen peroxide was calculated according to the following formula:

$$\text{Effective utilization rate} = \frac{M_{catechol} + M_{hydroquinone}}{M_{hydrogen\ peroxide\ charged}}$$

After used for 10 times, the catalyst was taken out, dried and calcined to obtain a white catalyst which was weighed and compared with the weight of the catalyst initially loaded, so as to calculate the retention rate of the catalyst:

$$\text{Retention rate} = \frac{m_{after\ 10\ cycles\ of\ reaction}}{m_{initially\ loaded}}$$

The reaction results are listed in the following table:

|  | Phenol Conversion | Effective Utilization Rate of $H_2O_2$ | Catalyst Retention Rate |
| --- | --- | --- | --- |
| Ex. 1 | 26.5% | 80.3% | 88.2% |
| Ex. 2 | 27.2% | 82.4% | 97.5% |
| Ex. 3 | 26.1% | 79.1% | 96.5% |
| Ex. 4 | 23.2% | 70.3% | 96.6% |

-continued

| | Phenol Conversion | Effective Utilization Rate of $H_2O_2$ | Catalyst Retention Rate |
|---|---|---|---|
| Ex. 5 | 22.8% | 69.1% | 92.3% |
| Ex. 6 | 28.1% | 85.2% | 94.5% |
| Ex. 7 | 26.1% | 79.1% | 98.8% |
| Comp. Ex. 1 | 28.2% | 85.5% | All passing through filter cloth |
| Comp. Ex. 2 | 21.3% | 64.5% | 76.8% |
| Comp. Ex. 3 | 20.3% | 61.5% | 98.1% |
| Comp. Ex. 4 | 26.8% | 81.2% | 65.3% |

As it can be seen from the evaluation results in the table, in comparison with the original titanium silicalite TS-1 powder, the catalytic activity of the microspherical titanium silicalite catalyst obtained by the conventional spray forming process was reduced significantly. Moreover, after used for 10 times in the reaction, the catalyst was damaged severely, and thus the fine catalyst powder passed through the filter cloth, leading to a large loss of the catalyst. In contrast, the catalytic activity of the spherical titanium silicalite catalyst prepared according to the present invention was notably higher than that of the catalyst prepared by the conventional technology, reaching the level of the original titanium silicalite TS-1 powder, with the phenol conversion and the effective utilization rate of hydrogen peroxide being similar. In addition, the loss of the catalyst was still very small after the catalyst was used for 10 cycles, indicating that the spherical titanium silicalite of the present invention has better mechanical strength and can maintain structural stability during long-term catalytic reaction.

What is claimed is:

1. A microspherical titanium silicalite catalyst having a composition of:

$$xTiO_2 \cdot (1-x)SiO_2/yMPO_4$$

wherein x=0.0005-0.04, y=0.005-0.2;

wherein M is a metallic element selected from alkaline earth metals, transition metals, or combinations of two or more thereof;

wherein the microspherical titanium silicalite catalyst is prepared as follows:

(i) providing an original titanium silicalite powder, wherein the original titanium silicalite powder has following composition:

$$xTiO_2 \cdot (1-x)SiO_2$$

wherein x=0.0005-0.04;

(ii) mixing a silica sol, an organic template and a phosphate at a molar ratio of 1:0.02-0.2:0.01-0.5 of $SiO_2$: organic template:phosphate to obtain a binder, wherein the phosphate is selected from alkaline earth metal phosphates, transition metal phosphates, or combinations of two or more thereof;

(iii) mixing the binder with the original titanium silicalite powder, spray-drying and firing at a temperature range of 350-600° C. to obtain the titanium silicalite catalyst, wherein when the binder is mixed with the original titanium silicalite powder, a weight ratio of silicon dioxide in the binder to the original titanium silicalite powder is 1:2-20.

2. The microspherical titanium silicalite catalyst of claim 1, wherein x=0.001-0.035; and y=0.008-0.15.

3. The microspherical titanium silicalite catalyst of claim 1, wherein M is selected from calcium, magnesium, zinc, nickel, aluminum, iron, copper, cobalt, or combinations of two or more thereof.

4. The microspherical titanium silicalite catalyst of claim 1, wherein based on $SiO_2$ in the silica sol, a molar ratio of the silica sol to the organic template is 1:0.04-0.18; and a molar ratio of the silica sol to the phosphate is 1:0.04-0.45.

5. The microspherical titanium silicalite catalyst of claim 1, wherein the organic template is selected from cetyltrimethylammonium bromide, cetyltriethylammonium bromide, cetyldiethylmethylammonium bromide, cetyltrimethylammonium chloride, cetyltriethylammonium chloride, cetyldiethylmethylammonium chloride, or mixtures thereof.

6. The microspherical titanium silicalite catalyst of claim 1, wherein based on a weight of silicon dioxide in the binder, a ratio of the binder to the original titanium silicalite powder is 1:4-18 when they are mixed.

7. The microspherical titanium silicalite catalyst of claim 1, wherein x=0.005-0.01; and y=0.03-0.05.

8. The microspherical titanium silicalite catalyst of a claim 1, wherein based on $SiO_2$ in the silica sol, a molar ratio of the silica sol to the organic template is 1:0.1-0.12; and a molar ratio of the silica sol to the phosphate is 1:0.15-0.3.

9. The microspherical titanium silicalite catalyst of claim 1, wherein based on a weight of silicon dioxide in the binder, a ratio of the binder to the original titanium silicalite powder is 1:10-12 when they are mixed.

10. A method for preparing a microspherical titanium silicalite catalyst, wherein the microspherical titanium silicalite catalyst has a composition of $$xTiO_2 \cdot (1-x)SiO_2/yMPO_4$$

wherein x=0.0005-0.04, y=0.005-0.2;

wherein M is selected from alkaline earth metals, transition metals, or combinations of two or more thereof;

wherein the method comprises:

(i) providing an original titanium silicalite powder, wherein the original titanium silicalite powder has following composition:

$$xTiO_2 \cdot (1-x)SiO_2$$

wherein x=0.0005-0.04;

(ii) mixing a silica sol, an organic template and a phosphate at a molar ratio of 1:0.02-0.2:0.01-0.5 of $SiO_2$: organic template:phosphate to obtain a binder, wherein the phosphate is selected from alkaline earth metal phosphates, transition metal phosphates, or combinations of two or more thereof;

(iii) mixing the binder with the original titanium silicalite powder, spray-drying and firing at a temperature range of 350-600° C. to obtain the titanium silicalite catalyst, wherein when the binder is mixed with the original titanium silicalite powder, a weight ratio of silicon dioxide in the binder to the original titanium silicalite powder is 1:2-20.

11. The method of claim 10, wherein x=0.001-0.035; and y=0.008-0.15.

12. The method of claim 10, wherein M is selected from calcium, magnesium, zinc, nickel, aluminum, iron, copper, cobalt, or combinations of two or more thereof; and the organic template is selected from cetyltrimethylammonium bromide, cetyltriethylammonium bromide, cetyldiethylmethylammonium bromide, cetyltrimethylammonium chloride, cetyltriethylammonium chloride, cetyldiethylmethylammonium chloride, or mixtures thereof.

13. The method of claim 10, wherein based on $SiO_2$ in the silica sol, a molar ratio of the silica sol to the organic template is 1:0.04-0.18; and a molar ratio of the silica sol to the phosphate is 1:0.04-0.45.

14. The method of claim 10, wherein based on a weight of silicon dioxide in the binder, a ratio of the binder to the original titanium silicalite powder is 1:4-18 when they are mixed.

15. The method of claim 10, wherein x=0.005-0.01; and y=0.03-0.05.

16. The method of claim 10, wherein based on $SiO_2$ in the silica sol, a molar ratio of the silica sol to the organic template is 1:0.1-0.12; and a molar ratio of the silica sol to the phosphate is 1:0.15-0.3.

17. The method of claim 10, wherein based on a weight of silicon dioxide in the binder, a ratio of the binder to the original titanium silicalite powder is 1:10-12 when they are mixed.

* * * * *